United States Patent [19]

Nagai et al.

[11] Patent Number: 4,676,106
[45] Date of Patent: Jun. 30, 1987

[54] ULTRASONIC TRANSDUCER

[75] Inventors: Yasutaka Nagai; Susumu Enjoji, both of Ootawara, Japan

[73] Assignee: Kabushiki Kaisha Toshiba, Kawasaki, Japan

[21] Appl. No.: 805,608

[22] Filed: Dec. 6, 1985

[30] Foreign Application Priority Data

Dec. 7, 1984 [JP] Japan .................. 59-257410

[51] Int. Cl.$^4$ ........................................... G01N 29/06
[52] U.S. Cl. ...................................... 73/625; 310/334
[58] Field of Search ................. 73/629, 632, 626, 625; 310/334, 335, 336, 327; 367/103, 105; 29/25.35

[56] References Cited

U.S. PATENT DOCUMENTS

| 3,952,387 | 4/1976 | Iinuma et al. | 310/334 |
| 4,385,255 | 5/1983 | Yamaguchi et al. | 310/335 |
| 4,424,465 | 1/1984 | Ohigashi et al. | 310/336 |
| 4,604,543 | 8/1986 | Umemura et al. | 310/334 |

Primary Examiner—Stephen A. Kreitman
Attorney, Agent, or Firm—Finnegan, Henderson, Farabow, Garrett & Dunner

[57] ABSTRACT

A phased-array ultrasonic transducer for an ultrasonograph is provided in which electrical signals are supplied to ultrasonic transducer elements to generate ultrasonic beams for diagnostic scanning. The ultrasonic transducer comprises a number of ultrasonic transducer elements arranged in the form of an array, a signal electrode plate coupled to the signal-supply side of the transducer elements and connected to a transmitter-receiver circuit by means of signal wires, and an earth electrode plate connected to the earth side of the transducer elements. The earth electrode plate is divided into a plurality of split earth electrode plates corresponding to ultrasonic transducer groups each including a plurality of adjacent transducer elements so that the split earth electrode plates are grounded independently. Thus, clearer and more accurate ultrasonic images can be obtained without undesired signals attributed to any other transducer elements than the transducer element in operation being produced or artifact appearing on the ultrasonic image.

7 Claims, 5 Drawing Figures

ULTRASONIC TRANSDUCER

BACKGROUND OF THE INVENTION

The present invention relates to an ultrasonic transducer used in ultrasonic imaging apparatus for medical diagnostics.

Generally, a phased-array ultrasonic transducer is constructed as shown in FIG. 4. In FIG. 4, numeral 1 designates a backing member shaped like a rectangular prism, and numeral 2 denotes a plurality of ultrasonic transducer elements arranged in an array. Metal electrode layers 2a and 2b are formed on the signal transmission surface side and signal supply surface side, respectively, of the transducer elements 2. Numeral 3 designates a signal electrode plate, one side edge of which is electrically connected to one side edge of the electrode layer 2b, and the other edge portion of which extends from one lateral face of the backing member 1 to the top side thereof. A plurality of signal pins 4 are arranged on the top-side portion of the signal electrode plate 3 so as to be connected to their corresponding transducer elements 2. Numeral 5 designates an acoustic convex lens provided on the transmission surface side of the ultrasonic transducer elements 2. Numeral 6 designates an earth electrode plate which extends over the other lateral face of the backing member 1, located on the earth side of the transducer elements 2. Connected to the metal electrode layer 2a, the earth electrode plate 6 serves as a common earth plate for the ultrasonic transducer elements 2. The signal pins 4 are connected individually to signal wires 7, which are shielded and electrically insulated by a shield member 8. The signal wires 7 are bound into a single bundle 9 at their shielded portions and connected to a transmitter-receiver circuit 10. The shield member of the bundle 9 is connected by soldering or the like to one end of a single and common grounding conductor 1 the other end of which is connected to the earth electrode plate 6.

FIG. 5 shows an equivalent circuit of the prior art ultrasonic transducer, in which a closed circuit is formed for each of transducer elements $2_1$ to $2_n$. For example, a driving pulser $10_A$ is connected to one end of the transducer element $2_1$, while a receiver circuit 10B is connected to each one end of the other transducer elements $2_n$. All the other ends of the transducer elements are grounded in common.

In the ultrasonic probe constructed in this manner, electrical pulses delivered from the transmitter-receiver circuit 10 are supplied to the transducer element $2_1$ through their corresponding signal line 7 for ultrasonic vibration, and are also transferred through the grounding conductor 1 and the earth electrode plate 6 to the grounding-conductor side of the shield members. Each of the shield members is connected to the single and common grounding conductor 1, so that part of the electrical pulse transferred from an operating transducer element is supplied to the other shield members 8 in addition to the shield member 8 for the wire that corresponds to the transducer element $2_1$ in operation. The above arrangement, in which the grounding terminals of the transducer elements are connected in common to the earth electrode plate 6 and the grounding conductor 1 is connected to the earth electrode plate 6, by itself has some impedance. This impedance does not permit the electrical signal fed, for example, to the transducer element $2_1$ by the driving pulser $10_A$ to be transmitted to the grounding conductor 1 in its entirety. Part of it is sent, via the electrode plate 6 to which the transducer elements are connected in common, to the adjacent transducer elements that are not intended to be in operation. Thus, the transducer elements that should not be in operation may operate erroneously. Furthermore, the ultrasonic transducer will transmit unnecessary pulses and receive unnecessary signals produced by transducer elements other than the transducer element in operation, resulting in artifacts in ultrasonic images and failing to provide accurate information on the region to be diagnosed.

SUMMARY OF THE INVENTION

The present invention is contrived in consideration of these circumstances, and is intended to provide an ultrasonic transducer for an ultrasonic imaging apparatus in which electrical signals are supplied to ultrasonic transducer elements to generate ultrasonic beams for ultrasonic beam scanning of an object, whereby accurate and clear ultrasonic images can be obtained without producing undesired signals attributed to any other transducer elements than the element in operation.

In order to achieve the above object, an ultrasonic transducer according to the present invention is provided which comprises a backing member; an array of ultrasonic transducer elements mounted on the backing member and formed into a plurality of groups, each of the groups including a plurality of ultrasonic transducer elements, each of the ultrasonic transducer elements having a signal-supply surface layer on a first face of the ultrasonic transducer element adjacent the backing member and a transmission surface side metal electrode layer on a second face of the ultrasonic transducer element opposite the first face; a signal electrode plate mounted to the backing member, the signal electrode plate having a plurality of first electrode lead means, each of the first electrode lead means being electrically coupled to one of the signal-supply surface side metal electrode layers; and an earth electrode plate mounted to the backing member, the earth electrode plate comprising a plurality of second electrode lead means, each of which is electrically coupled to the respective transmisssion surface side metal electrode layers of the ultrasonic transducer elements comprising one of the groups and grounded independently of others of the second electrode lead means, thereby providing a common ground potential for the transmission surface side metal electrode layers of the ultrasonic transducer elements comprising one of the groups independent of the ground potential of others of the groups.

DETAILED DESCRIPTION OF THE PREFERRED EMBODIMENT

Figure 1:
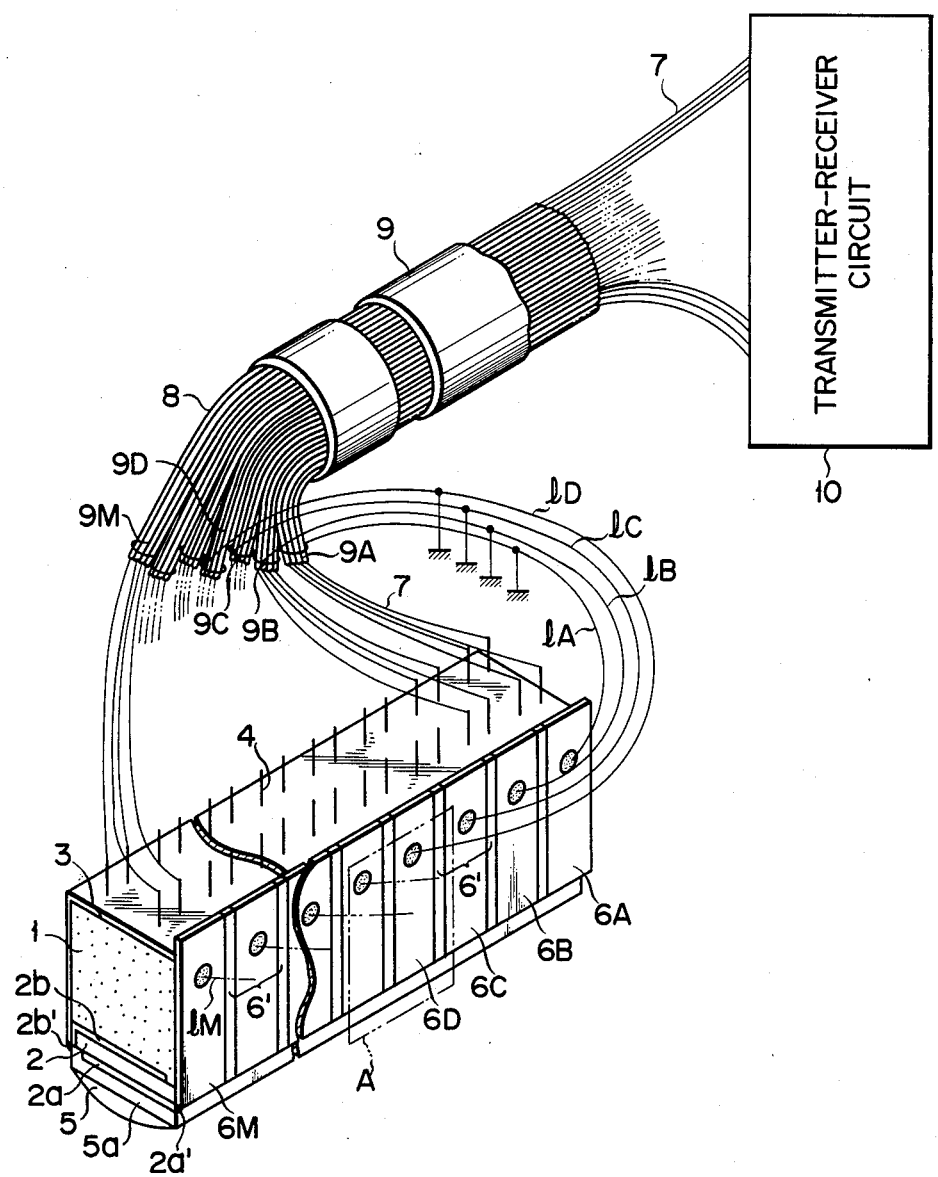
FIG. 1 is a perspective view showing an outline of an ultrasonic transducer according to an embodiment of the present invention.
Figure 2:
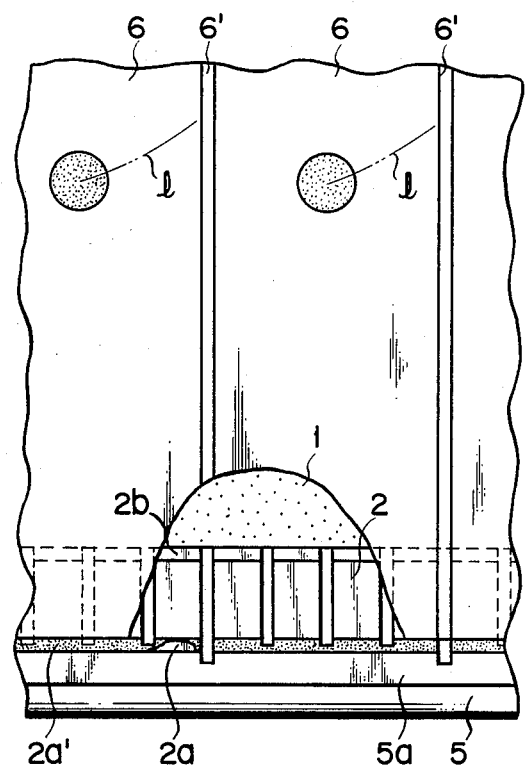
FIG. 2 is an enlarged front view showing part of the ultrasonic transducer as shown by the area marked as A in FIG. 1.
Figure 3:
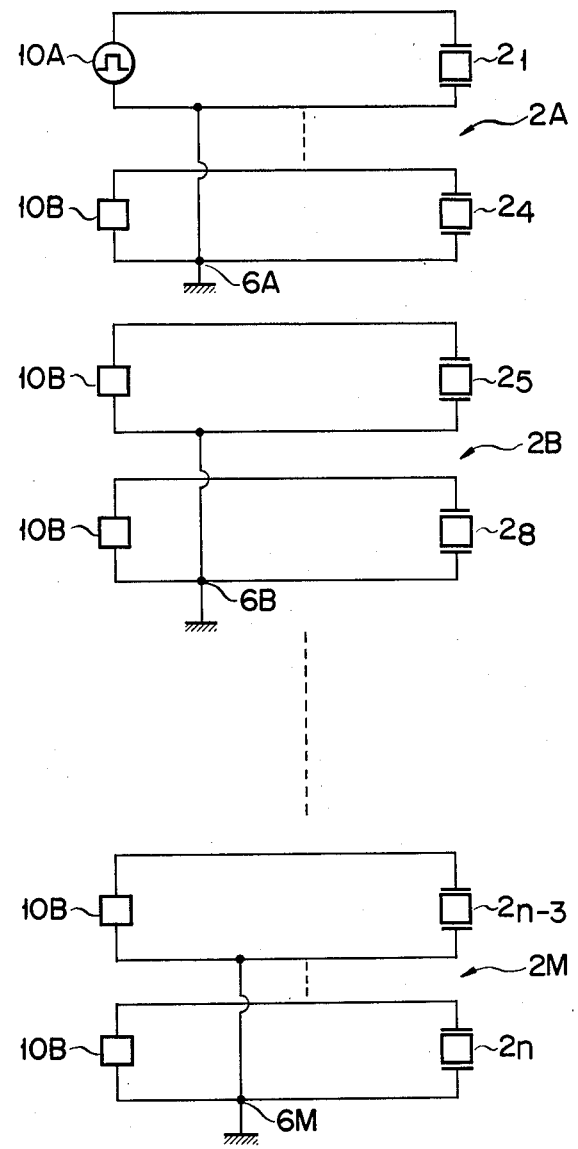
FIG. 3 is an equivalent circuit diagram of the ultrasonic transducer of FIG. 1.
Figure 4:
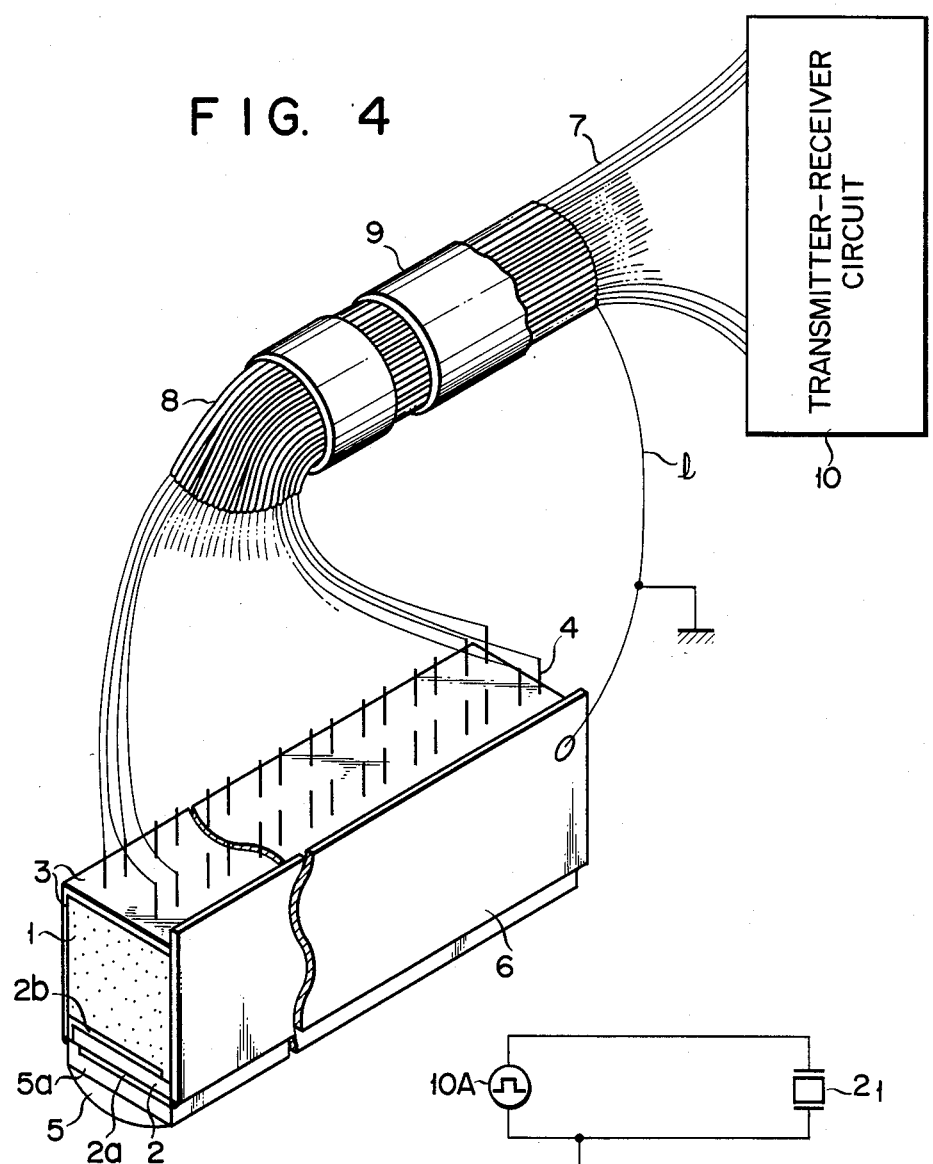
FIG. 4 is a perspective view showing an outline of a prior art ultrasonic transducer.
Figure 5:
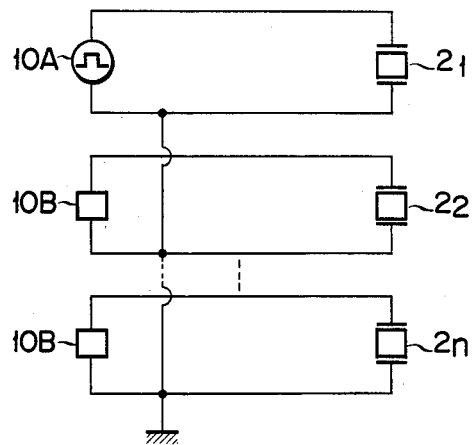
FIG. 5 is an equivalent circuit diagram of the ultrasonic transducer of FIG. 4.

FIGS. 1 to 3 show an ultrasonic transducer according to an embodiment of the present invention and its equivalent circuit. In these drawings, like reference numerals are used to designate like portions as included in the prior art ultrasonic transducer shown in FIGS. 4 and 5.

In FIG. 1, numeral 1 designates a backing member, and 2 denotes a plurality of transducer elements arranged in an array on the bottom face of the backing member 1. Metal electrode layers $2a$ and $2b$ are formed on the transmission surface side and signal-supply surface side, respectively, of the transducer elements 2. Numeral 3 designates a signal electrode plate which extends over one lateral face and the top face of the backing member 1. One side edge (lower side edge as illustrated) of the signal electrode plate 3 is bonded to the metal electrode layer $2b$ by means of, e.g., a layer $2b'$ formed of conductive bonding material and electrically connected to the transducer elements 2. Also, a matching layer $5a$ bonded to metal electrode layer $2a$ on the transmission surface side of the transducer elements 2 and an acoustic convex lens 5 bonded to the outside of the matching layer $5a$ are shown.

A plurality of split earth electrode plates $6_A$ to $6_M$ are arranged on the other lateral face of the backing member 1, divided in the direction of arrangement of the transducer elements 2. The electrode plates $6_A$ to $6_M$ are insulated from one another and independently grounded by means of grounding conductors $1_A$ to $1_M$, respectively, each having one end edge bonded to the metal electrode layer $2a$ on the transducer elements 2 by means of a layer $2a'$ of conductive bonding material. As shown in FIG. 2, a plurality of groups $2_A$ to $2_M$ each including a plurality of adjacent transducer elements are arranged corresponding to the earth electrode plates $6_A$ to $6_M$, respectively. The layer $2a'$ connecting the electrode plates and the transducer groups is divided into electrically isolated sections by slits each corresponding to two adjacent transducer groups and which extend to the matching layer $5a$. The insulating portion $6'$ of each of the split earth electrode plates $6_A$ to $6_M$ is in alignment vertically with each slit. Thus, the adjacent transducer groups $2_A$ to $2_M$ are connected as independent units to their corresponding split earth electrode plates $6_A$ to $6_M$ and grounded.

Shielded signal wires 7, which are connected to the signal electrode plate 3 by means of signal pins 4, are tied up in bundles for their corresponding transducer groups $2_A$ to $2_M$ and connected, in the form of bundles $9_A$ to $9_M$, to a transmitter-receiver circuit 10. Also, the shielding wire binding cables $9_A$ to $9_M$ are connected to their corresponding split earth electrode plates $6_A$ to $6_M$ by means of the grounding conductors $1_A$ to $1_M$ and grounded independently. There may be any number of split earth electrode plates $6_A$ to $6_M$. If the total number of transducer elements is 128, for example, the elements will preferably be divided into 32 blocks each including four transducer elements. In this case, there are as many shielding wire binding cables as there are transducer groups.

FIG. 3 shows the equivalent circuit of the above ultrasonic transducer, in which a closed circuit is formed for each of the vibrator blocks $2_A$ to $2_M$ ($2_1 \ldots 2_4$ to $2_{n-3} \ldots 2_n$) and a driving pulser $10_A$ and a receiver circuit $10_B$ are connected to each closed circuit. The transducer groups $2_A$ to $2_M$ are connected to the split earth electrode plates $6_A$ to $6_M$, respectively.

In the ultrasonic transducer of the present invention, as described above, a number of transducer elements arranged in an array are divided into blocks each including a plurality of adjacent transducer elements. The transducer groups are connected individually to split earth electrode plates insulated from one another, and the electrode plates $6_A \ldots 6_M$ are connected individually to the bundles $9_A \ldots 9_M$ corresponding to the transducer groups via grounding conductors $1_A \ldots 1_M$, and are grounded independently. Accordingly, for example, an electrical pulse supplied through a signal electrode plate is transferred only through the circuit of that transducer group $2_A$ which includes a transducer element $2_1$ in operation, and the earth current is prevented from flowing through the circuits of the other transducer groups $2_B$, $2_C \ldots 2_M$. Thus, there is no possibility of undesired signals attributable to transducer elements other than the operating element, or artifacts appearing in the ultrasonic image. A plurality of electric pulses in different phases may be supplied to the respective elements to obtain an electrically focused ultrasonic beam.

As compared with prior art ultrasonographs, an ultrasonograph using the ultrasonic transducer of the invention can provide clearer images and more accurate information on the region which is being diagnosed. The number of transducer elements constituting each transducer group may be varied according to the total number of transducer elements used. The number of split earth electrode plates depends on the number of the transducer groups used.

What is claimed is:
1. An ultrasonic transducer for transmitting ultrasonic pulses and receiving echoes of the ultrasonic pulses, comprising:
   a backing member;
   an array of ultrasonic transducer elements mounted on said backing member and formed into a plurality of groups, each of said groups including a plurality of ultrasonic transducer elements, each of said ultrasonic transducer elements having a signal-supply surface side metal electrode layer on a first face of said ultrasonic transducer element adjacent said backing member and a transmission surface side metal electrode layer on a second face of said ultrasonic transducer element opposite said first face;
   a signal electrode plate mounted to said backing member, said signal electrode plate having a plurality of first electrode lead means, each of said first electrode lead means being electrically coupled to one of said signal-supply surface side metal electrode layers; and
   an earth electrode plate mounted to said backing member, said earth electrode plate comprising a plurality of second electrode lead means, each of said second electrode lead means being electrically coupled to said respective transmission surface side metal electrode layers of said ultrasonic transducer elements comprising one of said groups and grounded independently of others of said second electrode lead means, thereby providing a common ground potential for said transmission surface side metal electrode layers of said ultrasonic transducer elements comprising one of said groups independent of the ground potential of others of said groups.

2. The ultrasonic transducer according to claim 1, wherein said second electrode lead means are electrically insulated from one another.

3. The ultrasonic transducer according to claim 1, wherein the first electrode lead means comprises a signal wire.

4. The ultrasonic transducer according to claim 1, wherein each of the second electrode lead means comprises a split earth electrode plate.

5. The ultrasonic transducer according to claim 4, wherein said split earth electrode plates are electrically insulated from one another.

6. The ultrasonic transducer according to claim 1, wherein each of the second electrode lead means comprises grounding conductor.

7. The ultrasonic transducer according to claim 6, wherein said grounding conductors are electrically insulated from one another.

* * * * *